(12) United States Patent
Wlassics et al.

(10) Patent No.: US 6,573,410 B2
(45) Date of Patent: Jun. 3, 2003

(54) IODINATION PROCESS

(75) Inventors: Ivan Wlassics, Genoa (IT); Vito Tortelli, Milan (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 10/140,996

(22) Filed: May 9, 2002

(65) Prior Publication Data

US 2002/0169276 A1 Nov. 14, 2002

(30) Foreign Application Priority Data

May 10, 2001 (IT) .......................... MI01A0954

(51) Int. Cl.⁷ .......................... C07C 41/22; C07C 41/48
(52) U.S. Cl. .................................... 568/615
(58) Field of Search ......................... 568/615

(56) References Cited

U.S. PATENT DOCUMENTS 5,117,055 A  *  5/1992  Abe et al. ...................... 544/98

FOREIGN PATENT DOCUMENTS

| EP | 0 348 948 | 1/1990 | ........... C08G/65/00 |
| EP | 0 520 821 | 12/1992 | ......... C07C/59/135 |

* cited by examiner

*Primary Examiner*—Rosalynd Keys
(74) *Attorney, Agent, or Firm*—Arent Fox Kintner Plotkin & Kahn PLLC

(57) ABSTRACT

A synthetic process of perfluoropolyether iodides, by reaction with LiI of monoacyl- or diacyl-halides of perfluoropolyethers, having number average molecular weight from 200 to 3,000, and having the following structure:

$$XCO-CF_2O[(CF_2O)_n(CF_2CF_2O)_m]_pCF_2-Q \quad (II)$$

wherein:
  m/n=0.5–10; p=0–20;
  X=Cl, F;
  Q=H, $CF_3$, X as above defined or COX', wherein X' is Cl, F with the proviso that X'=X;
  said process being characterized in that the iodination reaction is carried out operating at a temperature from 180° C. to 260° C.

6 Claims, No Drawings

IODINATION PROCESS

The present invention relates to a process for the iodination of perfluoropolyether acylhalides having the formula:

$$XCO\text{—}CF_2O[(CF_2O)_n(CF_2CF_2O)_m]_pCF_2\text{—}Q \quad (II)$$

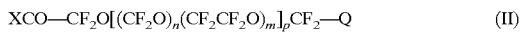

wherein X, Q and the indexes have the values defined hereunder to obtain perfluoropolyethers having iodinated —CF$_2$I end groups with high yields.

The iodinated perfluoropolyethers are usable as oleohydro-repellent compounds, or as components for preparing fluororesins, fluoroelastomers; or used as precursor of fluorinated surfactants.

Methods to iodinate perfluoropolyether acylhalides are known in the prior art, but having repeating units different from those of formula (II).

The iodination is for example carried out by reacting an acylfluoride with iodine in the presence of a perhalogenated solvent and of an alkaline or alkaline-earth metal carbonate, as described for example in EP 348,948. As an example of perhalogenated solvent hexachloro-1-3-butadiene is mentioned. The drawback of this process is that hexachloro-1-3-butadiene is not a solvent usable from an industrial point of view since it is an irritating compound.

Another process for preparing iododerivatives of perfluoropolyethers having a structure different from that shown in (II) is reported in EP 520,821 which describes the reaction of an acylfluoride with a metal iodide, wherein the metal is for example Li, Na, Mg, Ca, Al, to form perfluoropolyethers having —COI end groups. According to this patent the reaction takes place at temperatures between 0° C. and 100° C., and in a subsequent step the irradiation of the obtained compound is carried out by UV rays at room temperature, obtaining the perfluoropolyether with iodinated end groups. The drawback of said process is to comprise two distinct steps and to use a UV ray source, which as well known requires rather complex plants to be industrially operated.

The need was felt to have available a process for preparing perfluoropolyethers having one or both the end groups with an iodine atom starting from linear perfluoropolyether monoacyl- or diacyl-halides, having structure (II), which allowed to obtain products having high yields, without substantially modifying the number average molecular weight $M_n$, of the starting product of structure (II), said average molecular weight being considered without the two —COX end groups.

An object of the present invention is a process for preparing perfluoropolyether iodides, by reaction with LiI of monoacyl- or diacyl-halides of perfluoropolyethers, having a number average molecular weight from 200 to 3,000, preferably from 500 to 3,000, still more preferably from 1,000 to 3,000, and having the following structure:

$$XCO\text{—}CF_2O[(CF_2O)_n(CF_2CF_2O)_m]_pCF_2\text{—}Q \quad (II)$$

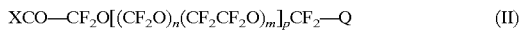

wherein:
m/n=0.5–10; p=0–20;
X=Cl, F;
Q=H, CF$_3$, X as above defined or COX', wherein X' is Cl, F with the proviso that X'=X;
said process being characterized in that the iodination reaction is carried out in a reactor, at a temperature from 180° C. to 260° C., preferably from 185° C. to 220° C.

The process of the present invention can operate both in the presence and in absence of solvents.

As solvents, those which solubilize the perfluoropolyethers of formula (II) are used. Acetonitrile, perfluorooctane, etc. can for example be mentioned.

Preferably in the process of the invention in formula (II) X=X'=F.

The ratio by moles between LiI and —OCF$_2$COX end groups ranges from 1.1 to 2.

The reaction time is that necessary to reach the total conversion of the perfluoropolyether halide in the corresponding iodide at the selected reaction temperature. Generally the reaction is considered over when in the reactor a pressure value is reached which remains constant at the selected reaction temperature. Generally reaction times of 4–6 hours are sufficient to end the reaction.

In the sealed reactor used in the process according to the present invention, before starting the reaction, the gases are removed by reducing the internal pressure.

The iodinated perfluoropolyether compounds obtained with the process of the invention have the following formula:

$$I\text{—}CF_2O[(CF_2O)_n(CF_2CF_2O)_m]_pCF_2\text{—}T \quad (I)$$

wherein T=I, F, CF$_3$, H, Cl; m/n=0.5–10, p=0–20 and having average number molecular weight from 200 to 3,000.

The results of the present invention are particularly surprising and unexpected since in the prior art the preparation of iodinated compounds of perfluoropolyethers having structure (I) has never been described. Indeed in the starting compounds of structure (II), —OCF$_2$O—units (Cl unit) in position β with respect to the —COX end group are present in the structure. When the structure of the fluorinated acylhalide compound comprises the aforesaid groups, contemporaneously with the iodination the secondary reaction of β-scission takes place. This causes the decrease of Cl units in the perfluoropolyether structure, with formation of carbonyl fluoride COF$_2$. Therefore the β-scission reaction causes a mass loss of the final product. It has been found by the Applicant that the effect of this secondary reaction is particularly evident when an iodinating agent different from LiI is used.

By operating with the process of the invention it has been unexpectedly found that the β-scission reaction can be remarkably reduced or substantially eliminated.

The following Examples illustrate the invention but they do not limit the scope thereof.

EXAMPLE 1a (COMPARATIVE)

Synthesis of the di-iodide derivative from perfluoro-oxy-diacylchloride of formula ClCOCF$_2$OCF$_2$COCl (corresponding to the general formula II wherein p=0) MW=243

20 grams of the diacylhalide (82.3 mmoles, 164 meq) are reacted with 40.8 grams of anhydrous, finely milled KI (246 mmoles, 1.5 moles KI/eq diacylchloride). KI is transferred into a 300 ml AISI 316 autoclave equipped with magnetic stirrer. The oxygen is removed from the autoclave inside by repeating two-three times the following cycle: vacuum formation by oil pump (residual vacuum about 10$^{-2}$ mm Hg) and subsequent washing with nitrogen. The autoclave under vacuum is charged by siphoning with perfluoro-oxy-diacylchloride, and then dipped in an oil bath, maintaining the mixture inside under strong stirring. The internal temperature of the autoclave is regulated at 210° C. by a thermocouple. The reaction time is calculated from the time when the internal temperature reaches 210° C. and it is of 4.5 hours. This time is determined by calculating the pressure theoretically obtainable at complete conversion of acylhalide by the standard gas law, and stopping the reaction when in the reactor the pressure is maintained constant around the calculated value. The pressure is measured by a manometer or a pressure reader placed at the autoclave head. The pressure increases during the reaction due to the gases which are released and which do not remain dissolved in the reaction mixture and fill the free volume of the autoclave. The free volume in the case of the present Example was 267 ml.

The maximum pressure reached at the end of the reaction was 22 atm.

At the end of the reaction the autoclave is connected to a vacuum line and the gases contained in the autoclave are collected and analyzed by GC-MS. The non gaseous content remained in the autoclave is collected and analyzed by $^{19}F$ NMR. The comparison between the analyses of the gases and of the products remained in the autoclave allows to precisely calculate the diacylchloride conversion, the di-iodide yield, and the β-scission, determined by the percentage of $COF_2$ by moles which has formed.

The conversion of the diacylchloride was 100% but the di-iodide yield was only 2% and the β-scission was 95%. The residual material was starting product and mono-iodinated product.

EXAMPLE 1b

Synthesis as in Example 1a of the di-iodide derivative from perfluoro-oxy-diacylfluoride of formula $FCOCF_2OCF_2COF$ MW=210 but using LiI instead of KI Example 1a is repeated using LiI instead of KI and the above mentioned perfluoro-oxy-diacylfluoride instead of perfluoro-oxy-diacylchloride. One operates at 210° C. for 5.5 hours.

The maximum pressure reached at the end of the reaction was 20 atm; the conversion was 100%, the di-iodide yield was 57% by moles and the β-scission was 43% by moles.

EXAMPLE 2 (COMPARATIVE)

Synthesis of the di-iodide derivative from perfluoro-oxy-diacylchloride of formula $ClCOCF_2[(CF_2O)_n(CF_2CF_2O)_m]_pCF_2COCl$ MW=600, m/n=2.2, p=1.2

50 grams of the diacylhalide (82.3 mmoles, 164 meq) have been reacted with 41 grams of anhydrous, finely milled KI (247 mmoles, 1.5 moles KI/eq diacylchloride). KI is transferred into a 300 ml AISI 316 autoclave equipped with a magnetic stirrer. The oxygen is removed from the autoclave inside by repeating for two-three times the following cycle: vacuum formation by oil pump and subsequent washing with nitrogen.

The autoclave under vacuum is charged by siphoning with perfluoro-oxy-diacylchloride, and then dipped in an oil bath, maintaining the mixture inside under strong stirring. The internal temperature of the autoclave is regulated at 210° C. by a thermocouple. The mixture is allowed to react at 210° C. for 8 hours. The maximum pressure, reached at the end of the reaction, is 22 atm.

At the end of the reaction the conversion was 100%, the di-iodide yield was 98% and the β-scission 15.

EXAMPLE 3

Example 2 is repeated but using LiI instead of KI and using a perfluoro-oxy-diacylfluoride of formula $FCOCF_2[(CF_2O)_n(CF_2CF_2O)_m]_pCF_2$ COF MW=570, m/n=2.2 p=1.2.

At the end of the reaction the conversion was 100%, the di-iodide yield was 98% and the β-scission lower than 1%.

EXAMPLE 4

Example 3 is repeated but using a perfluoro-oxy-diacylfluoride having MW 1,100, m/n=2.5 p=5.

At the end of the reaction the conversion was 100%, the di-iodide yield was 98% and the β-scission lower than 1%.

EXAMPLE 5

Example 3 is repeated but using a perfluoro-oxy-diacylfluoride having MW 3,000, m/n=1.7 p=15.

At the end of the reaction the conversion was 100%, the in di-iodide yield was 98% and the β-scission lower than 1%.

EXAMPLE 6 (COMPARATIVE)

Iodination of perfluoropolyethers of formula (II) with $Ag_2O$ and iodine according to U.S. Pat. No. 3,810,874

A perfluoropolyether diacid having formula: $HOOC-CF_2O[(CF_2O)_n(CF_2CF_2O)_m]_p-CF_2COOH$ with m/n=2.5 and p=5 is allowed to react with an equivalent amount of $Ag_2O$ forming the silver salt and subsequently with an equivalent amount of iodine, at the temperature of 120° C., under the Hunsdiecker reaction conditions. At the end of the reaction the analysis of the compound by $^{19}F$ NMR analysis shows only traces of iodinated end groups, the almost totality of the other end groups being acid and non reactive.

What is claimed is:

1. A process for preparing perfluoropolyether iodides, by reaction with LiI of monoacyl- or diacyl-halides of perfluoropolyethers, having number average molecular weight from 200 to 3,000, and having the following structure:

$$XCO-CF_2O[(CF_2O)_n(CF_2CF_2O)_m]_pCF_2-Q \qquad (II)$$

Wherein:
m/n=0.5–10;
p=0–20;
X=Cl, F;
Q=H, $CF_3$, X as above or COX', wherein X' is Cl, F with the proviso that X'=X;
said process being characterized in that the iodination reaction is carried out at a temperature from 180° C. to 260° C.

2. A process according to claim 1, wherein one operates in the presence of solvents.

3. A process according to claim 2, wherein the used solvents are those which solubilize the perfluoropolyethers of formula (II).

4. A process according to claim 1, wherein in formula (II) X=X'=F.

5. A process according to claim 1, wherein the ratio by moles between LiI and $-OCF_2COX$ end groups ranges from 1.1 to 2.

6. A process according to claim 1 wherein the iodination reaction is carried out at a temperature from 185° C. to 220° C.

* * * * *